United States Patent
Fujiwara

(10) Patent No.: US 10,101,308 B2
(45) Date of Patent: Oct. 16, 2018

(54) REFRACTIVE INDEX DETECTOR AND LIQUID CHROMATOGRAPH

(71) Applicant: SHIMADZU CORPORATION, Kyoto-shi, Kyoto (JP)

(72) Inventor: Masanori Fujiwara, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 180 days.

(21) Appl. No.: 15/074,000

(22) Filed: Mar. 18, 2016

(65) Prior Publication Data
US 2016/0274074 A1    Sep. 22, 2016

(30) Foreign Application Priority Data

Mar. 19, 2015  (JP) .................................. 2015-056781

(51) Int. Cl.
| | | |
|---|---|---|
| G01N 21/05 | (2006.01) | |
| G01N 21/41 | (2006.01) | |
| G01N 30/74 | (2006.01) | |

(52) U.S. Cl.
CPC ............. *G01N 30/74* (2013.01); *G01N 21/05* (2013.01); *G01N 21/41* (2013.01); *G01N 2201/061* (2013.01); *G01N 2201/068* (2013.01)

(58) Field of Classification Search
None
See application file for complete search history.

(56) References Cited

U.S. PATENT DOCUMENTS

| | | | | |
|---|---|---|---|---|
| 5,398,110 A | * | 3/1995 | Kitaoka ............. | G01N 21/4133 356/130 |
| 6,063,284 A | * | 5/2000 | Grill .................. | B01D 15/1814 210/198.2 |
| 6,295,125 B1 | * | 9/2001 | Tokieda ............. | G01N 21/4133 356/130 |
| 8,322,197 B2 | * | 12/2012 | Koster ................... | G01N 30/20 73/61.55 |
| 2007/0076192 A1 | * | 4/2007 | Nakamura ......... | G01N 21/4133 356/131 |
| 2008/0024770 A1 | * | 1/2008 | Nakamura ............. | G01N 21/05 356/130 |
| 2010/0147086 A1 | | 6/2010 | Koster et al. | |

(Continued)

FOREIGN PATENT DOCUMENTS

| | | |
|---|---|---|
| CN | 101113950 A | 1/2008 |
| JP | 2006-162262 A | 6/2006 |

*Primary Examiner* — Manish S Shah
*Assistant Examiner* — Jean Morello
(74) *Attorney, Agent, or Firm* — Westerman, Hattori, Daniels & Adrian, LLP

(57) ABSTRACT

An embodiment of a refractive index detector includes a sample cell, a reference cell, a measurement section, a liquid inlet port, liquid outlet sections, and a switching mechanism. The inlet port leads to a sample cell inlet. A first outlet port and a second outlet port are for discharging a liquid. The switching mechanism includes a reference liquid supply mode for forming a channel for connecting a reference cell outlet to one of the first outlet port and the second outlet port while connecting a sample cell outlet to a reference cell inlet, and an analysis mode for forming a channel for connecting the sample cell outlet to one of the first outlet port and the second outlet port while sealing the reference cell outlet.

12 Claims, 11 Drawing Sheets

(56) References Cited

U.S. PATENT DOCUMENTS

2013/0067997 A1* 3/2013 Ebsen .................... G01N 30/20
73/61.55
2016/0018326 A1* 1/2016 Jeanotte ................ G01N 21/05
356/130

* cited by examiner

REFRACTIVE INDEX DETECTOR AND LIQUID CHROMATOGRAPH

BACKGROUND OF THE INVENTION

1. Field of the Invention

The present invention relates to a refractive index detector for detecting a refractive index difference between a sample cell through which a sample flows and a reference cell containing a reference liquid, based on the behavior of light which has passed through the sample cell and the reference cell, and for measuring the concentration of a sample flowing through the sample cell based on the refractive index difference, and a liquid chromatograph that uses the refractive index detector.

2. Description of the Related Art

A refractive index detector is used by a liquid chromatograph as a detector for detecting a sample component separated by an analytical column. The refractive index detector includes a sample cell and a reference cell that are provided being separated from each other by a partition wall, and causes a sample solution to flow in the sample cell in a state where a reference liquid (a solvent not containing the sample) is contained in the reference cell, and measures the behavior of light which has passed through the sample cell and the reference cell at this time. The optical path of the transmission light changes according to the refractive index difference between the sample cell and the reference cell. Accordingly, if the amount of displacement from a reference position of the slit image of the transmission light is detected, the concentration of the sample flowing through the sample cell may be determined.

Such a refractive index detector generally includes one inlet port and one outlet port for connecting pipes, and switches, by a switching valve, between whether a liquid supplied from the inlet port is to flow along the route of sample cell-reference cell-outlet port, or along the route of sample cell-outlet port (for example, see FIG. 3 of JP 2006-162262A). In the case of causing the liquid to flow along the route of sample cell-outlet port, the outlet of the reference cell is closed.

When supplying a reference liquid to the reference cell, a solvent not containing a sample is caused to flow, as a reference liquid, along the route of sample cell-reference cell-outlet port, and the reference cell is filled with the reference liquid. After the reference cell is filled with the reference liquid, the switching valve is switched so that the liquid flows along the route of the sample cell-outlet port, and the sample concentration in the sample solution flowing through the sample cell is detected based on the refractive index difference between the sample cell and the reference cell.

SUMMARY OF THE INVENTION

A liquid discharged from the outlet port of the refractive index detector is normally discarded directly to a drain or via a mass spectrometer or the like. However, in cases such as where using an expensive solvent, a solvent, in the solvent to be discharged from the outlet port, not containing a sample is desirably returned to the original solvent container to be reused. In such a case, a switching valve has to be separately added to a later stage side of the refractive index detector, and switching has to be performed by the switching valve between whether a liquid that is discharged from the outlet port is to be returned to the solvent container or not. Then, the switching valve inside the refractive index detector and the switching valve that is separately provided on the later stage side are simultaneously controlled, and thus, control is complicated. Moreover, since an external switching valve has to be provided, there are problems that the cost and the installation area are increased. Furthermore, when an external switching valve is provided, a dead volume is increased by this amount, and there is a problem that, in the case where a detector such as a mass spectrometer is connected immediately after the switching valve, the sample component is diffused, thereby affecting the analysis result.

A refractive index detector according to the present invention includes a sample cell, a reference cell, a measurement section, an inlet port, a first outlet port, a second outlet port, and a switching mechanism. The sample cell is a light transmitting container, and includes a sample cell inlet through which a liquid flows in, and a sample cell outlet through which a liquid flows out. The reference cell is also a light transmitting container, and includes a reference cell inlet through which a liquid flows in, and a reference cell outlet through which a liquid flows out. The sample cell and the reference cell are arranged adjacent to each other across a light transmitting partition wall. The measurement section includes a light source and a photodetector. The light source emits light in such a way that the light passes through both of the sample cell and the reference cell from a side of one of the cells. The photodetector detects displacement of the light which has passed through the sample cell and the reference cell. A liquid inlet port leads to the sample cell inlet. The first outlet port and the second outlet port are provided to discharge a liquid to the outside. The switching mechanism includes a reference liquid supply mode and an analysis mode. The reference liquid supply mode is a mode for connecting the reference cell outlet to either the first outlet port or the second outlet port while connecting the sample cell outlet to the reference cell inlet. The analysis mode is a mode for connecting the sample cell outlet to either the first outlet port or the second outlet port while sealing the reference cell outlet.

According to such a structure, the refractive index detector of the present invention may selectively discharge, from either the first outlet port or the second outlet port, a liquid which has passed through the sample cell, or a liquid which has passed through the sample cell and the reference cell. Accordingly, if a recycle channel leading to the original solvent container is connected to either the first outlet port or the second outlet port, a solvent may be returned to the solvent container as necessary without using a separate switching valve. Since there is no need to use an external switching valve, the cost and the installation area are not increased, and control is not complicated. Since an external switching valve is not used, even if a detector such as a mass spectrometer is provided at a later stage of the refractive index detector, the dead volume between the refractive index detector and the detector at the later stage side is small, and influence of diffusion of a sample on analysis may be made small.

A liquid chromatograph according to the present invention includes a delivery pump, an analysis channel, a sample introduction section, an analytical column, the refractive index detector described above, and a recycle channel. The delivery pump suctions a solvent from a solvent container storing the solvent, and delivers the solvent. The analysis channel delivers, as a mobile phase, the solvent suctioned from the solvent container by the delivery pump. The sample introduction section is provided on the analysis channel, on a downstream side of the delivery pump, and introduces a sample into the analysis channel. The analytical column is provided on the analysis channel, on a downstream side of the sample introduction section, and separates the sample introduced into the analysis channel by the sample introduction section into sample components. The recycle channel is a channel connecting the second outlet port of the refractive index detector and the solvent container, and is for returning a liquid flowing out of the second outlet port to the solvent container.

According to such a structure, the liquid chromatograph according to the present invention may return, as necessary, a solvent which has passed through the refractive index detector to the solvent container and may reuse the solvent, without increasing the cost and the installation area.

DETAILED DESCRIPTION OF THE INVENTION

Figure 1:
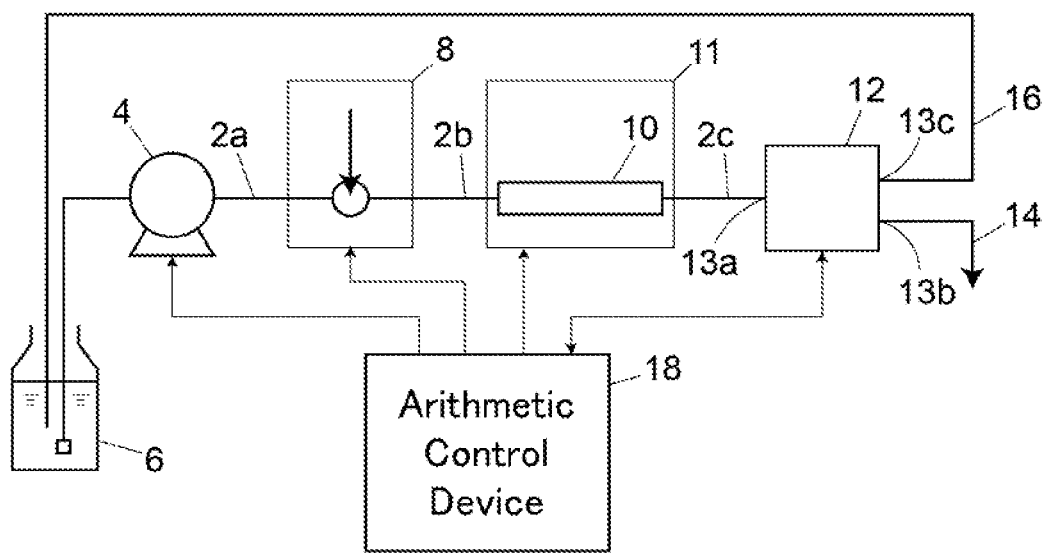
FIG. 1 is a schematic configuration diagram showing an example of a liquid chromatograph.

A switching mechanism of a refractive index detector of the present invention may be configured from one rotary switching valve.

As an example of the switching valve to be used as the switching mechanism, one may be cited that includes ports to which a sample cell outlet, a reference cell inlet, a reference cell outlet, a first outlet port, and a second outlet port are connected, and a rotor that is provided with grooves for connecting the ports, and that switches the connection between the ports by rotating.

As such a switching valve, one may be cited that includes one center port and a plurality of circumferential ports arranged on a circumference having the center port as a center, where the rotor includes two grooves provided in a circumferential direction so as to connect adjacent ports of the circumferential ports, and one groove provided in a radial direction so as to connect the center port and one of the circumferential ports.

The switching valve may have the sample cell outlet, the reference cell inlet, the reference cell outlet, and the first outlet port connected to the circumferential ports, have the second outlet port connected to the center port, and have the reference cell inlet and the first outlet port connected to ports adjacent to the port to which the sample cell outlet is connected, and the port to which the reference cell outlet is connected and the port to which the first outlet port is connected may be adjacent to each other.

A recycle channel for returning a liquid to a liquid supply section is desirably connected to the second outlet port. In this case, the switching mechanism desirably has, as reference liquid supply modes, a reference liquid normal supply mode and a reference liquid recycled supply mode, and has, as analysis modes, a normal analysis mode and a recycle analysis mode. The reference liquid normal supply mode is a mode in which the sample cell outlet is connected to the reference cell inlet, and the reference cell outlet is connected to the first outlet port. The reference liquid recycled supply mode is a mode in which the sample cell outlet is connected to the reference cell inlet, and the reference cell outlet is connected to the second outlet port. The normal analysis mode is a mode in which the reference cell outlet is sealed, and the sample cell outlet is connected to the first outlet port. The recycle analysis mode is a mode in which the reference cell outlet is sealed, and the sample cell outlet is connected to the second outlet port. With the switching mechanism having these modes, whether a reference liquid flowing out of the reference cell outlet is to be returned to the liquid supply section at the time of supply of the reference liquid to the reference cell, and whether a solvent is to be returned to the liquid supply section at the time of analysis may be switched by the switching mechanism. Thus, a solvent may be reused at the time of supply of a reference liquid to the reference cell and at the time of analysis.

According to a preferred embodiment, a control section for controlling an operation of the switching mechanism is provided. In this case, the control section desirably includes a recycle analysis operation section for placing, based on a detection signal of a photodetector of a measurement section, the switching mechanism in the normal analysis mode when a sample is detected during analysis of the sample, and in the recycle analysis mode when a sample is not detected. Then, at the time of analysis, a solution containing a sample and a solution not containing a sample may be discharged from separate outlet ports, and only the solution not containing a sample may be returned to the liquid supply section through the recycle channel.

An example of a liquid chromatograph will be described with reference to FIG. 1.

According to the liquid chromatograph of the present example, a delivery pump 4, an autosampler 8 (sample injection section), an analytical column 10, and a detector 12 are serially connected by channels 2a, 2b, and 2c, and form an analysis channel for performing separation/analysis of a sample.

The delivery pump 4 suctions a solvent from a solvent container 6 at a set flow rate, and delivers the solvent. The autosampler 8 is connected to the outlet side of the delivery pump 4 by the channel 2a. The autosampler 8 automatically collects a sample in a sample container set by a user, and injects the sample into an analysis channel. The solvent delivered by the delivery pump 4 flows through the analysis channel. The analytical column 10 is connected to the outlet side of the autosampler 8 by the channel 2b. The analytical column 10 is accommodated inside a column oven 11. The analytical column 10 is for separating the sample injected by the autosampler 8 into components. The detector 12 is connected to the outlet side of the analytical column 10 by the channel 2c, and a sample component separated by the analytical column 10 is detected by the detector 12.

The detector 12 is a refractive index detector provided with a sample cell through which a sample solution flows and a reference cell containing a reference liquid. The detector 12 detects the sample concentration in the sample solution flowing through the sample cell based on the behavior of light which has passed through the sample cell and the reference cell. The detector 12 includes one inlet port 13a, and two outlet ports 13b and 13c (hereinafter, the outlet port 13b will be referred to as a first outlet port, and the outlet port 13c as a second outlet port).

The inlet port 13a of the detector 12 is connected to the analytical column 10 by the channel 2c. An outlet channel 14 is connected to the first outlet port 13b. A recycle channel 16 is connected to the second outlet port 13c. The outlet channel 14 may directly lead to a drain, or a detector such as a mass spectrometer may be further connected thereto. The recycle channel 16 is a channel for returning a solvent which has passed through the detector 12 to the solvent container 6. The detector 12 is provided with a switching mechanism for switching between which of the first outlet port 13b and the second outlet port 13c a liquid flowing from the inlet port 13a is to be discharged from.

The delivery pump 4, the autosampler 8, the column oven 11, and the detector 12 are modularized, and the operations of the modules are managed by an arithmetic control device 18 in a centralized manner. The arithmetic control device 18 is configured by, for example, a general-purpose personal computer or a dedicated computer. A user inputs, by the arithmetic control device 18, analysis conditions such as the delivery flow rate of a solvent and a temperature condition of the column oven. The arithmetic control device 18 controls the operations of the delivery pump 4, the autosampler 8, the column oven 11, and the detector 12 based on the input conditions, and also performs various arithmetic processes such as determination of the concentration of a sample component based on a detection signal obtained by the detector 12.

An example of the detector 12 will be described with reference to the schematic diagram in FIG. 2.

A sample cell 20 and a reference cell 22 are provided. The sample cell 20 and the reference cell 22 both have a triangular cross section, and are arranged adjacent each other across a partition wall 24. The sample cell 20, the reference cell 22, and the partition wall 24 are made of a light transmitting material. The sample cell 20 includes a sample cell inlet $S_{in}$ through which a liquid flows in, and a sample cell outlet $S_{out}$ through which the liquid flows out, and the reference cell 22 includes a reference cell inlet $R_{in}$ through which a liquid flows in, and a reference cell outlet $R_{out}$ through which the liquid flows out. The sample cell inlet $S_{in}$ is connected to the inlet port 13a by a channel 30. The sample cell outlet $S_{out}$, the reference cell inlet $R_{in}$, and the reference cell outlet $R_{out}$ are connected to ports of a rotary switching valve 42 by respective channels 32, 34, and 36. Details of the switching valve 42 will be given later.

A light source 26 and a photodetector 28 are provided as a measurement section for detecting a sample concentration in a solution flowing through the sample cell 20. In the drawing, only the light source 26 and the photodetector 28 are shown for the sake of convenience, but a slit is arranged on the optical path of light from the light source 26, and an optical system for forming, on the photodetector 28, a slit image of the light which has passed through the sample cell 20 and the reference cell 22 is also provided. The photodetector 28 is a photodiode array having a plurality of detection elements arranged in an array. The photodetector 28 detects the amount of displacement of the slit image that is formed on the photodetector 28.

Figure 2:
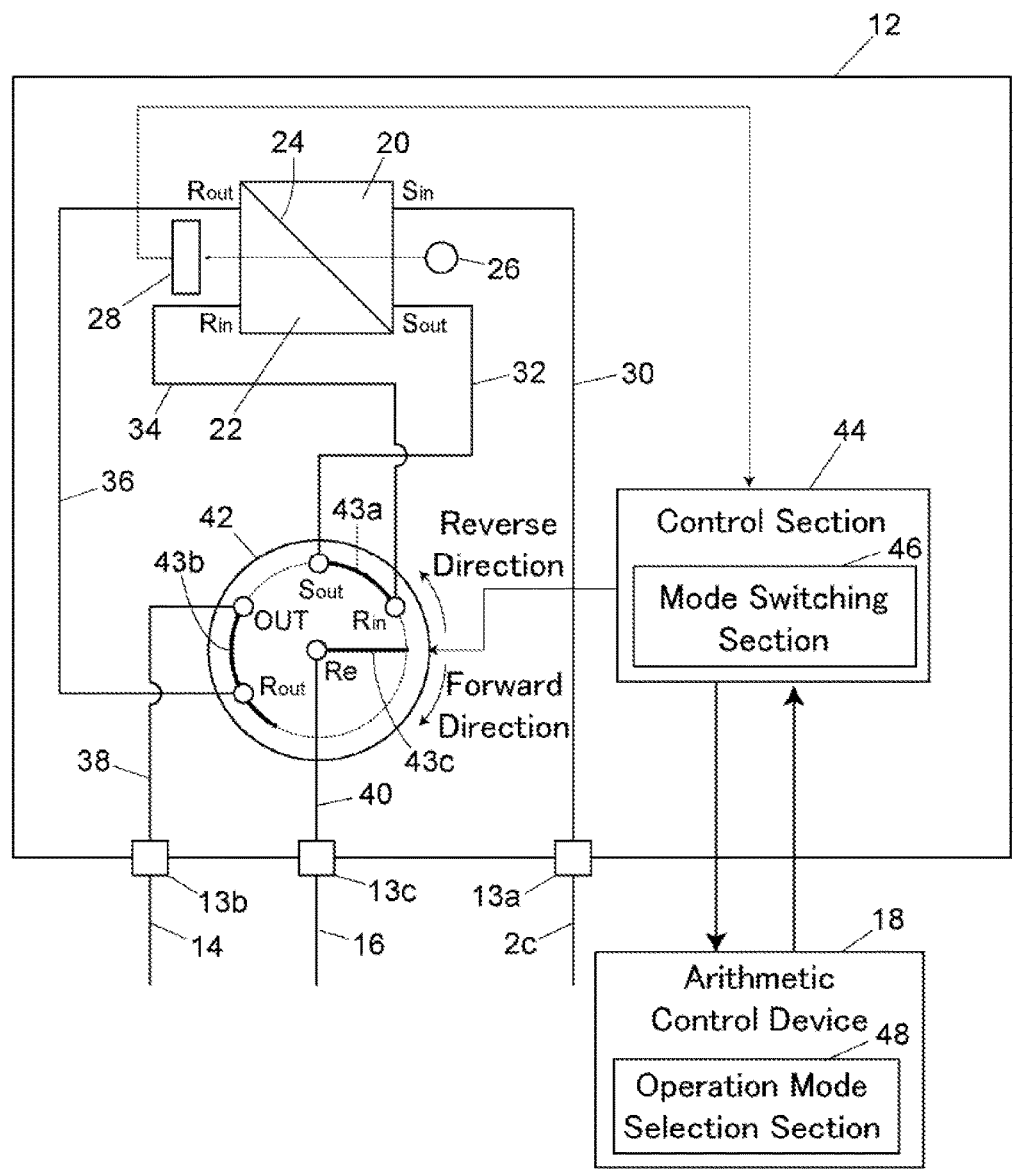
FIG. 2 is a schematic configuration diagram showing a detector according to the present example.

In FIG. 2, the photodetector 28 is shown being arranged opposite the light source 26 across the sample cell 20 and the reference cell 22, but, for example, the photodetector 28 may be provided on the same side as the light source 26, and the amount of displacement of light which has been reflected by a mirror provided opposite the light source 26 across the sample cell 20 and the reference cell 22 and which has passed again through the sample cell 20 and the reference cell 22 may be detected by the photodetector 28.

The switching valve 42 includes one center port (hereinafter referred to as "port (Re)") that communicates with the second outlet port 13c by a channel 40. The switching valve 42 further includes, on the same circumference having the center port (Re) as the center, four circumferential ports, namely, a port (hereinafter referred to as "port ($R_{in}$)") that communicates with the reference cell inlet $R_{in}$ by the channel 34, a port (hereinafter referred to as "port ($S_{out}$)") that communicates with the sample cell outlet $S_{out}$ by the channel 32, a port (hereinafter referred to as "port (OUT)") that communicates with the first outlet port 13b by a channel 38, and a port (hereinafter referred to as "port ($R_{out}$)") that communicates with the reference cell outlet $R_{out}$ by the channel 36.

The four circumferential ports are provided on the circumference having the center port (Re) as the center, in the order, in the counterclockwise direction, of the port ($R_{in}$), the port ($S_{out}$), the port (OUT), and the port ($R_{out}$). In the following description, the clockwise direction on the circumference, of the switching valve 42, having the center port (Re) as the center will be referred to as a forward direction, and the counterclockwise direction will be referred to as a reverse direction, as shown in FIG. 2.

The port ($S_{out}$) is provided at a position that is rotated from the position of the port ($R_{in}$) by 60 degrees in the reverse direction around the center port (Re), the port (OUT) at a position that is rotated from the position of the port ($S_{out}$) by 60 degrees in the reverse direction around the center port (Re), and the port ($R_{out}$) at a position that is rotated from the position of the port (OUT) by 60 degrees in the reverse direction around the center port (Re).

The switching valve 42 includes a rotor that rotates around the center port (Re). The rotor is provided with three grooves 43a, 43b, and 43c for connecting between the ports. The grooves 43a and 43b of the rotor are provided on the circumferential direction of the circle where the circumferential ports are provided, and the groove 43c is provided in the radial direction of the circle. The groove 43a has a length of a 60-degree arc around the center port (Re). The groove 43b has a length of a 90-degree arc around the center port (Re). An end portion of the groove 43b in the forward direction is provided with a space, equivalent to a 60-degree arc around the center port (Re), from an end portion of the groove 43a in the reverse direction. One end of the groove 43c is provided at a position corresponding to the center port (Re), and the other end is provided at a position, on the circumference where the circumferential ports are provided, shifted by 30 degrees in the forward direction from an end portion of the groove 43a in the forward direction. The grooves 43a and 43b form channels for communicating between two adjacent circumferential ports. The groove 43c forms a channel for communicating between the center port (Re) and one of the circumferential ports.

The switching valve 42 is a switching mechanism that includes, as reference liquid supply modes for supplying a reference liquid to the reference cell 22, (1) a reference liquid normal supply mode and (2) a reference liquid recycled supply mode, and as analysis modes for analyzing a sample, (3) a normal analysis mode and (4) a recycle analysis mode.

Additionally, the structures of the switching valve forming the switching mechanism, particularly, the number and positions of the ports, and the shapes and combination of the grooves provided to the rotor, are not limited to the present example.

In the following, each of the modes (1) to (4) will be described with reference to FIGS. 3 to 6.

Figure 3:
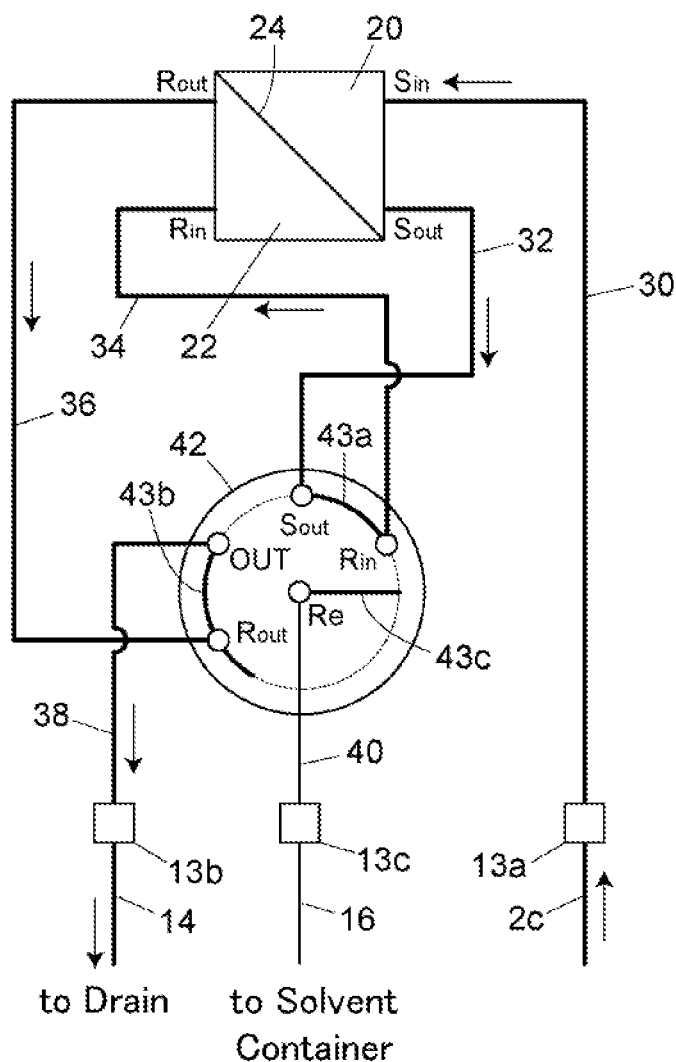
FIG. 3 is a diagram showing a channel structure of the detector at the time of a reference liquid normal supply mode.

(1) Reference Liquid Normal Supply Mode (See FIG. 3)

The reference liquid normal supply mode is a mode of a channel structure according to which a solvent not containing a sample is supplied to the reference cell 22 as a reference liquid, and a solvent flowing out of the reference cell 22 is discharged to the drain, by routes indicated by thick lines in FIG. 3. At the switching valve 42, the port ($S_{out}$) and the port ($R_{in}$) are communicated by the groove 43a, and the port (OUT) and the port ($R_{out}$) are communicated by the groove 43b. At this time, the center port (Re) is not connected by the groove 43c to any of the circumferential ports.

In the reference liquid normal supply mode, a solvent in the solvent container 6 delivered by the delivery pump 4 flows into the sample cell inlet $S_{in}$ through the channel 2c, the inlet port 13a, and the channel 30, and after flowing through the sample cell 20, the solvent is supplied to the reference cell 22 via the sample cell outlet $S_{out}$, the channel 32, the port ($S_{out}$), the groove 43a, the port ($R_{in}$), the channel 34, and the reference cell inlet $R_{in}$. The solvent flowing out of the reference cell outlet $R_{out}$ filling the reference cell 22 is discharged to the drain via the channel 36, the port ($R_{out}$), the groove 43b, the port (OUT), the channel 38, the first outlet port 13b, and the channel 14. Then, the switching valve 42 is switched to a state where the port ($R_{out}$) is not connected to any of the other ports, and the state where the reference cell 22 is filled with the reference liquid may be maintained, and analysis of a sample is performed by causing a sample solution to flow through the sample cell 20 in this state (see FIGS. 5 and 6).

Figure 4:
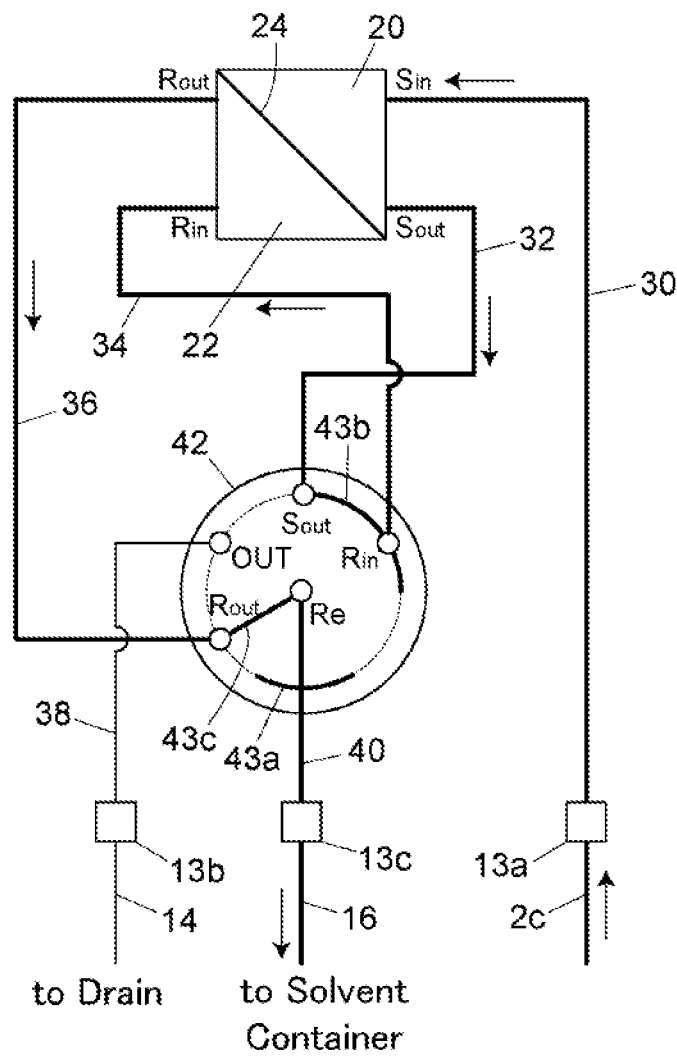
FIG. 4 is a diagram showing a channel structure of the detector at the time of a reference liquid recycled supply mode.

(2) Reference Liquid Recycled Supply Mode (See FIG. 4)

The reference liquid recycled supply mode is a mode for a case such as where an expensive solvent is used, for example, according to which, when a solvent as a reference liquid is being supplied to the reference cell 22, the solvent flowing out of the reference cell 22 may be reused. In this mode, a channel structure is used according to which a solvent not containing a sample is supplied to the reference cell 22 as a reference liquid, and a solvent flowing out of the reference cell 22 is returned to the solvent container 6, by routes indicated by thick lines in FIG. 4. At the switching valve 42, the port ($S_{out}$) and the port ($R_{in}$) are communicated by the groove 43b, and the port ($R_{out}$) and the center port (Re) are communicated by the groove 43c.

In the reference liquid recycled supply mode, a solvent delivered through the channel 2c as a reference liquid flows into the sample cell inlet $S_{in}$ through the inlet port 13a and the channel 30, and after flowing through the sample cell 20, the solvent is supplied to the reference cell 22 via the sample cell outlet $S_{out}$, the channel 32, the port ($S_{out}$), the groove 43a, the port ($R_{in}$), the channel 34, and the reference cell inlet $R_{in}$. The solvent flowing out of the reference cell outlet $R_{out}$ after filling the reference cell 22 is returned to the solvent container 6 via the channel 36, the port ($R_{out}$), the groove 43c, the center port (Re), the channel 40, the second outlet port 13c, and the recycle channel 16. Then, the switching valve 42 is switched to a state where the port ($R_{out}$) is not connected to any of the other ports, and the state where the reference cell 22 is filled with the reference liquid may be maintained, and analysis of a sample is performed by causing a sample solution to flow through the sample cell 20 in this state (see FIGS. 5 and 6).

Figure 5:
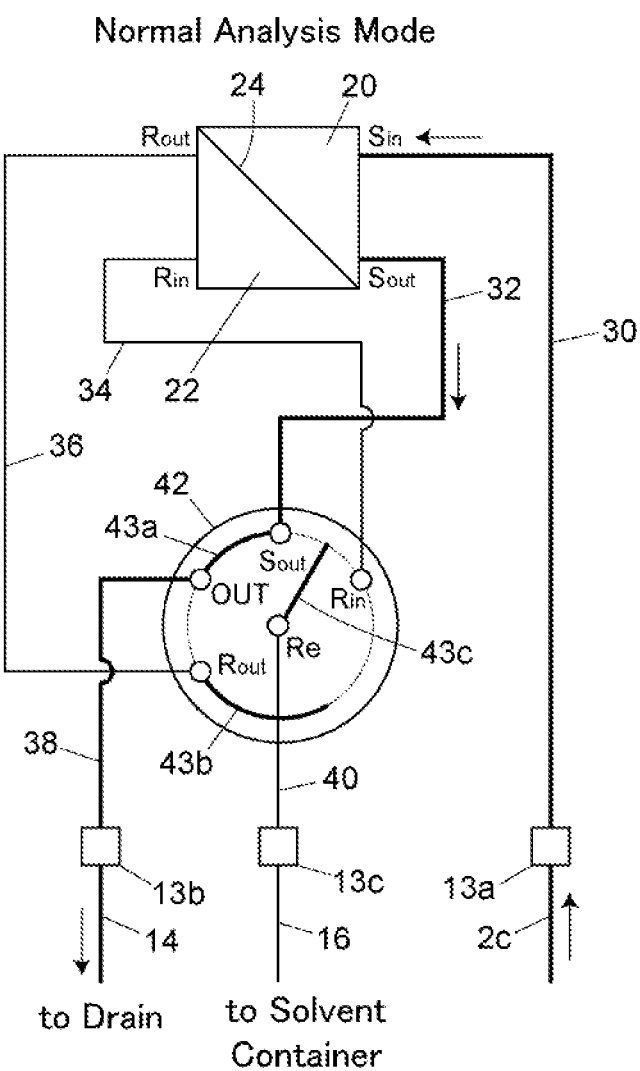
FIG. 5 is a diagram showing a channel structure of the detector at the time of a normal analysis mode.

(3) Normal Analysis Mode (See FIG. 5)

The normal analysis mode is a mode for analyzing a sample by causing, after the reference liquid supply mode of (1) or (2) described above, a sample solution to flow only on the side of the sample cell 20. At the switching valve 42, the port ($S_{out}$) and the port (OUT) are communicated by the groove 43a. At this time, the port ($R_{out}$) is not connected to any of the other ports, and the reference cell 22 is maintained in a state where it is filled with the reference liquid.

In the normal analysis mode, a solvent or a sample solution delivered through the channel 2c flows into the sample cell inlet $S_{in}$ through the inlet port 13a and the channel 30, and after flowing through the sample cell 20, the solvent or the sample solution is discharged to the drain via the sample cell outlet $S_{out}$, the channel 32, the port ($S_{out}$), the groove 43a, the port (OUT), the channel 38, the first outlet port 13b, and the channel 14.

Figure 6:
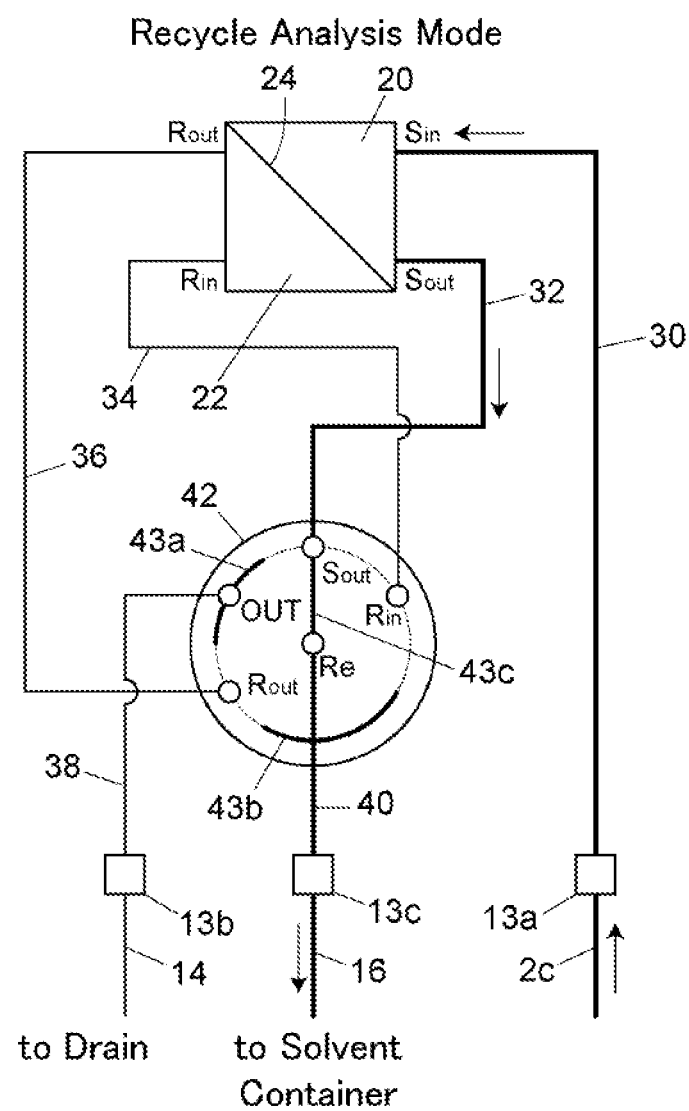
FIG. 6 is a diagram showing a channel structure of the detector at the time of a recycle analysis mode.

(4) Recycle Analysis Mode (See FIG. 6)

As in the normal analysis mode of (3) described above, the recycle analysis mode is a mode for analyzing a sample by causing, after the reference liquid supply mode of (1) or (2) described above, a sample solution to flow only on the side of the sample cell 20. The recycle analysis mode is used in combination with the normal analysis mode of (3) described above in a case such as where an expensive solvent is used, and is a mode for reusing a solvent (not containing a sample component) flowing out of the sample cell 20 during analysis. At the switching valve 42, the port ($S_{out}$) and the center port (Re) are communicated by the groove 43c. At this time, the port ($R_{out}$) is not communicated with any of the other ports, and the reference cell 22 is maintained in a state where it is filled with the reference liquid.

In the recycle analysis mode, a liquid delivered through the channel 2c flows into the sample cell inlet $S_{in}$ through the inlet port 13a and the channel 30, and after flowing through the sample cell 20, the liquid is returned to the solvent container 6 via the sample cell outlet $S_{out}$, the channel 32, the port ($S_{out}$), the groove 43c, the center port (Re), the channel 40, the second outlet port 13c, and the recycle channel 16.

Returning to FIG. 2, the detector 12 includes a control section 44 for controlling the operation of the switching valve 42. The control section 44 is capable of communicating information with the arithmetic control device 18 controlling the operation of the entire liquid chromatograph. The control section 44 is provided with a mode switching section 46 for switching the switching valve 42 among the modes (1) to (4) based on an operation condition input by a user to the arithmetic control device 18. The arithmetic control device 18 is provided with an operation mode selection section 48 for allowing a user to select, before an analysis operation for a sample is started, whether supply of a reference liquid to the reference cell 22 is to be performed in the normal mode (see FIG. 3) or in the recycle mode (see FIG. 4), and whether the recycle mode (see FIG. 6) is to be used or not at the time of analysis of a sample.

The control section 44 is configured from an arithmetic device such as a CPU, and a storage device storing programs, and the mode switching section 46 is a function that is realized by a program and the arithmetic device executing the program. The operation mode selection section 48 of the arithmetic control device 18 is a function that is realized by a program stored in a storage device provided to the arithmetic control device 18 and an arithmetic device such as a CPU executing the program.

Figure 7:
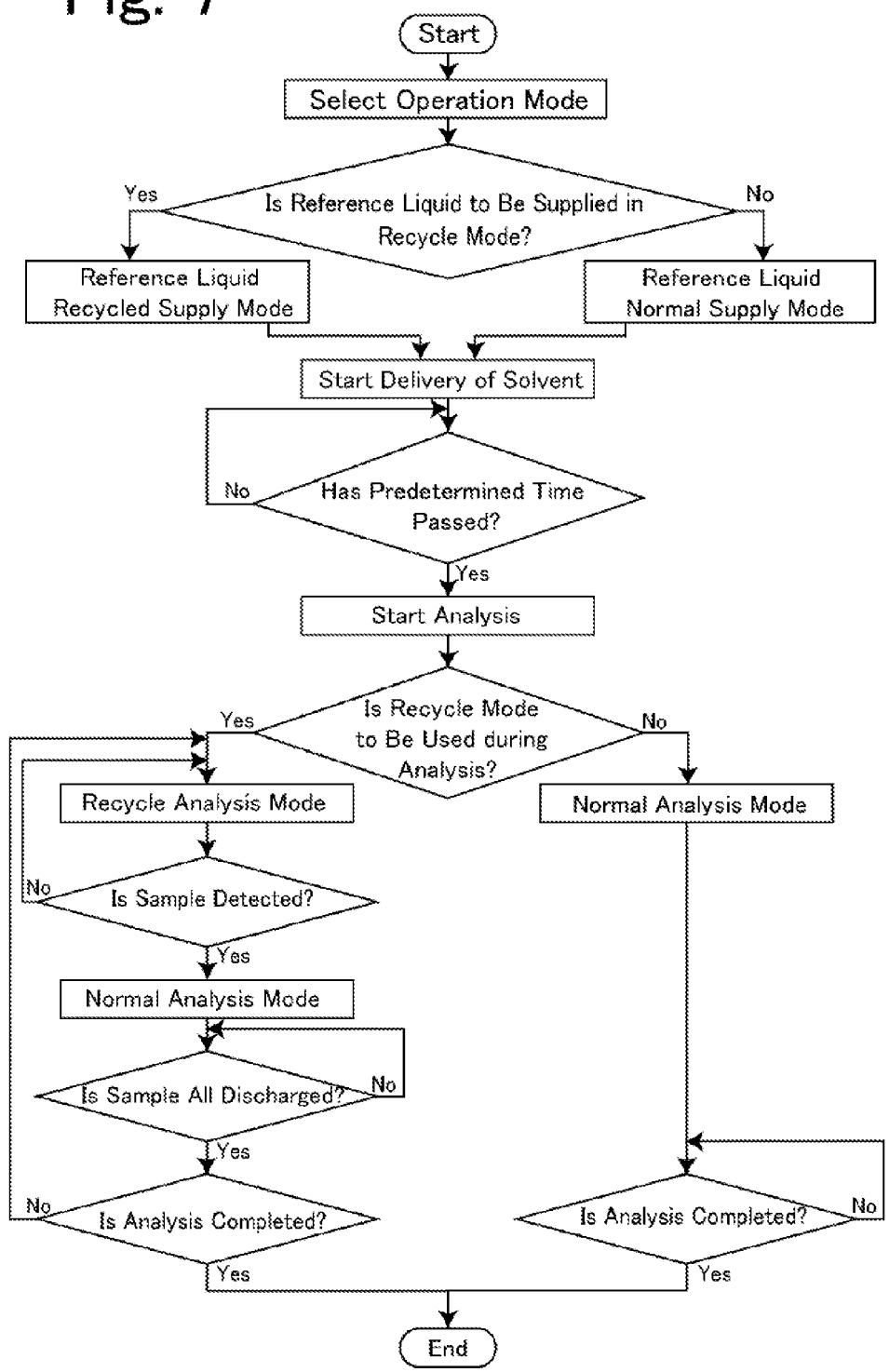
FIG. 7 is a flow chart showing an analysis operation according to the present example.

The flow of the present example from supply of a reference liquid to analysis of a sample will be described with reference to FIG. 7.

As an example, an operation mode selection screen is displayed on a display connected to the arithmetic control device 18, and a user is made to select an operation mode, that is, whether supply of a reference liquid to the reference cell 22 is to be performed in the normal mode (see FIG. 3) or in the recycle mode (see FIG. 4), and whether the recycle mode (see FIG. 6) is to be used at the time of analysis of a sample or not.

In the case where supply of a reference liquid in the recycle mode is selected, the switching valve 42 is placed in the reference liquid recycled supply mode (see FIG. 4), and delivery of a solvent by the delivery pump 4 is started. A reference liquid is thereby supplied to the reference cell 22, and the reference liquid overflowing from the reference cell 22 is returned to the solvent container 6 via the recycle channel 16. On the other hand, in the case where supply of a reference liquid in the normal mode is selected, the switching valve 42 is placed in the reference liquid normal supply mode (see FIG. 3), and delivery of a solvent by the delivery pump 4 is started. A reference liquid is supplied to the reference cell 22, but the reference liquid overflowing from the reference cell 22 is discharged to the drain via the channel 14. Analysis of a sample is started after a predetermined time has passed from the start of supply of the reference liquid to the reference cell 22, and the sample is injected by the autosampler 8 into the analysis channel where the solvent is flowing.

In the case where use of the recycle mode is selected for analysis, the switching valve 42 is placed in the recycle analysis mode (see FIG. 6) from immediately after the start of analysis to detection of a flow of a sample component into the sample cell 20. A solvent not containing the sample component is thereby returned to the solvent container 6 via the recycle channel 16. Detection of the sample component is performed by detection of displacement of a slit image of light from the light source 26 formed on the photodetector 28.

When a flow of the sample component into the sample cell 20 is detected, the switching valve 42 is switched to the normal analysis mode (see FIG. 5) immediately after the detection or after the lapse of a preset time (time until the sample component reaches the switching valve 42) from detection of the flow of the sample component into the sample cell 20, and the solvent containing the sample is discharged to the drain via the channel 14. Further, in the case where a mass spectrometer is connected to the channel 14, discharge to the drain is performed after further analysis is performed at the mass spectrometer. When the sample component is no longer detected in the sample cell 20, and there is no more sample component on the upstream side of the port ($S_{out}$), the switching valve 42 is placed again in the recycle analysis mode (see FIG. 6) until the next sample component is detected, and the solvent not containing the sample is returned to the solvent container 6. Such an operation is repeatedly performed until the end of analysis.

In the case where non-use the recycle mode is selected for analysis, the switching valve 42 is placed in the normal analysis mode (FIG. 5) until the end of the analysis. In this case, both a solvent containing a sample and a solvent not containing the sample are discharged to the drain via the channel 14.

An example of another configuration of the detector 12 will be described with reference to FIGS. 8 to 11.

In the present example, a switching valve 142 is used instead of the switching valve 42. The switching valve 142 includes one center port (hereinafter referred to as "port ($S_{out}$)") that communicates with a sample cell outlet S a channel 32. The switching valve 142 further includes, on the same circumference having the center port ($S_{out}$) as the center, five circumferential ports, namely, a port (hereinafter referred to as "port ($R_{in}$)") that communicates with a reference cell inlet $R_{in}$, a port (hereinafter referred to as "port ($S_{out}$)") that communicates with an outlet port, a port (hereinafter referred to as "port (OUT1)") that communicates with an outlet port 13*b* by a channel 38*a*, a port (hereinafter referred to as "port (OUT2)") that communicates with the outlet port 13*b* by a channel 38*b*, a port (hereinafter referred to as "port ($R_{out}$)") that communicates with a reference cell outlet $R_{out}$ by a channel 36, and a port (hereinafter referred to as "port (Re)") that communicates with a second outlet port 13*c* by a channel 40. The channels 38*a* and 38*b* are merged along the way, and are both connected to the first outlet port 13*b*.

The five circumferential ports are provided on the circumference having the center port ($S_{out}$) as the center, in the order, in the clockwise direction, of the port ($R_{in}$), the port (OUT1), the port (Re), the port ($R_{out}$), and the port (OUT2). In the following description, the clockwise direction on the circumference, of the switching valve 142, having the center port ($S_{out}$) as the center will be referred to as a forward direction, and the counterclockwise direction will be referred to as a reverse direction.

The port (OUT1) is provided at a position that is rotated from the position of the port ($R_{in}$) by 60 degrees in the forward direction around the center port ($S_{out}$), the port (Re) at a position that is rotated from the position of the port (OUT1) by 60 degrees in the forward direction around the center port ($S_{out}$), the port ($R_{out}$) at a position that is rotated from the position of the port (Re) by 60 degrees in the forward direction around the center port ($S_{out}$), and the port (OUT2) at a position that is rotated from the position of the port ($R_{out}$) by 60 degrees in the forward direction around the center port ($S_{out}$).

Three grooves 143*a*, 143*b*, and 143*c* for connecting between the ports are provided to a rotor of the switching valve 142. The grooves 143*a* and 143*b* of the rotor are provided on the circumferential direction of the circle where the circumferential ports are provided, and the groove 143*c* is provided in the radial direction of the circle. The groove 143*a* has a length of a 30-degree arc around the center port ($S_{out}$). The groove 143*b* has a length of a 90-degree arc around the center port ($S_{out}$). An end portion of the groove 143*b* in the forward direction is provided with a space, equivalent to a 120-degree arc around the center port ($S_{out}$), from an end portion of the groove 143*a* in the reverse direction. One end of the groove 143*c* is provided at a position corresponding to the center port ($S_{out}$), and the other end is provided at a position of an end portion of the groove 143*a* in the forward direction. That is, the grooves 143*a* and 143*c* are communicated with each other.

As in the example of using the switching valve 42, by switching of the switching valve 142, channels for realizing four modes, namely, a reference liquid normal supply mode (see FIG. 8), a reference liquid recycled supply mode (see FIG. 9), a normal analysis mode (see FIG. 10), and a recycle analysis mode (see FIG. 11), may be formed, and a liquid chromatograph may perform a similar operation (see FIG. 7) as in the example where the switching valve 42 is used.

Figure 8:
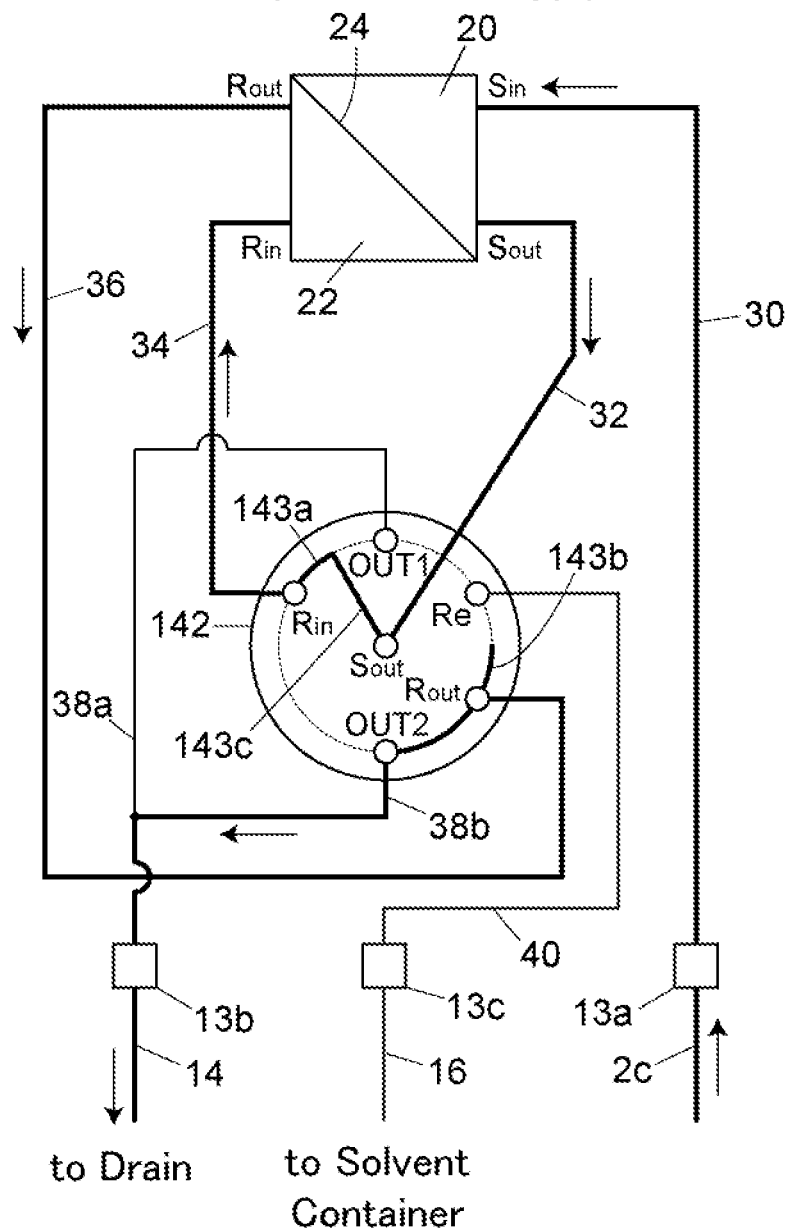
FIG. 8 is a diagram showing a channel structure of another example of the detector at the time of the reference liquid normal supply mode.

As shown in FIG. 8, channels for the reference liquid normal supply mode are formed by placing an end portion of the groove 143a in the reverse direction at the position of the port ($R_{in}$), communicating the center port ($S_{out}$) and the port ($R_{in}$) by the grooves 143a and 143c, and communicating the port ($R_{out}$) and the port (OUT2) by the groove 143b. As shown by thick lines in FIG. 8, according to such a channel structure, a solvent flowing out of a sample cell 20 flows into a reference cell 22 via the channel 32, the groove 143c, the groove 143a, and a channel 34, and a solvent flowing out of the reference cell 22 is discharged to a drain via the channel 36, the groove 143b, the channel 38, the first outlet port 13b, and a channel 14.

Figure 9:
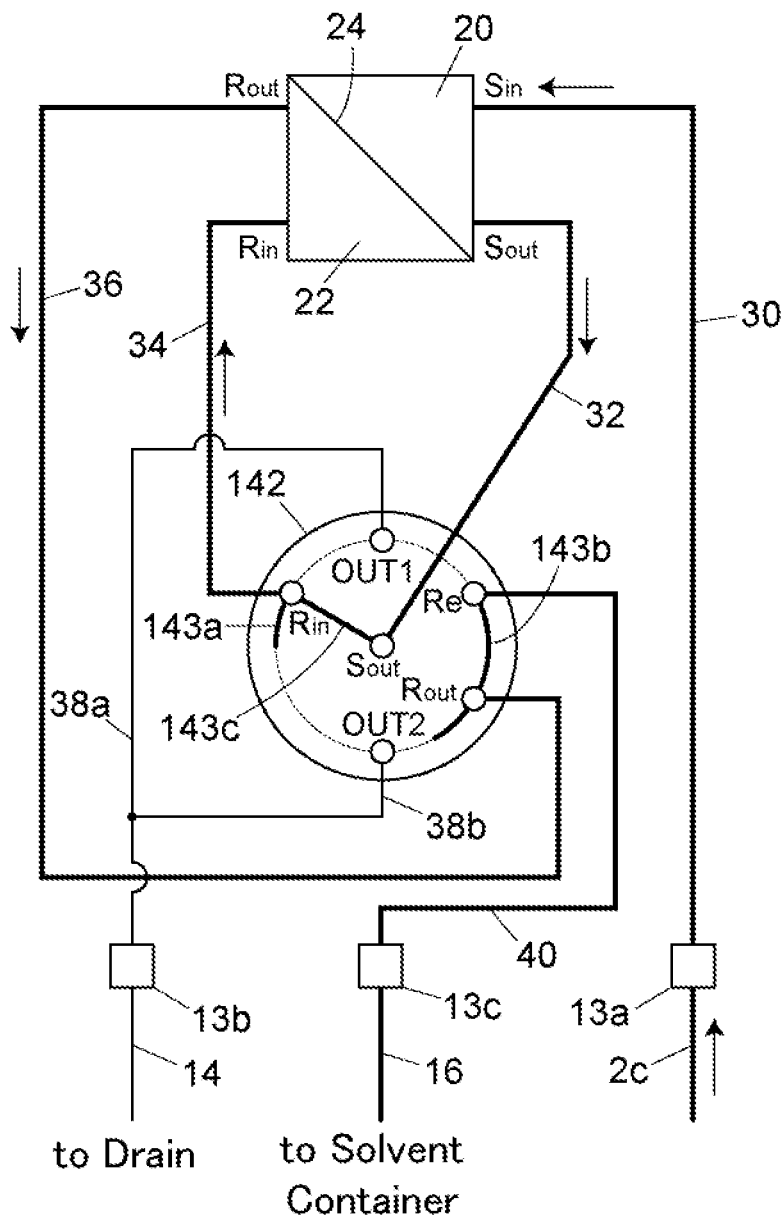
FIG. 9 is a diagram showing a channel structure of the present example at the time of the reference liquid recycled supply mode.

As shown in FIG. 9, channels for the reference liquid recycled supply mode are formed by rotating the rotor of the switching valve 142 by 30 degrees in the reverse direction from the state of the reference liquid normal supply mode, and by placing the end portion of the groove 143a in the forward direction at the position of the port ($R_{in}$), communicating the center port ($S_{out}$) and the port ($R_{in}$) by the groove 143c, and communicating the port ($R_{out}$) and the port (Re) by the groove 143b. As shown by thick lines in FIG. 9, according to such a channel structure, a solvent flowing out of the sample cell 20 flows into the reference cell 22 via the channel 32, the groove 143c, the groove 143a, and a channel 34, and a solvent flowing out of the reference cell 22 is returned to a solvent container 6 via the channel 36, the groove 143b, the channel 40, the second outlet port 13b, and a recycle channel 16.

Figure 10:
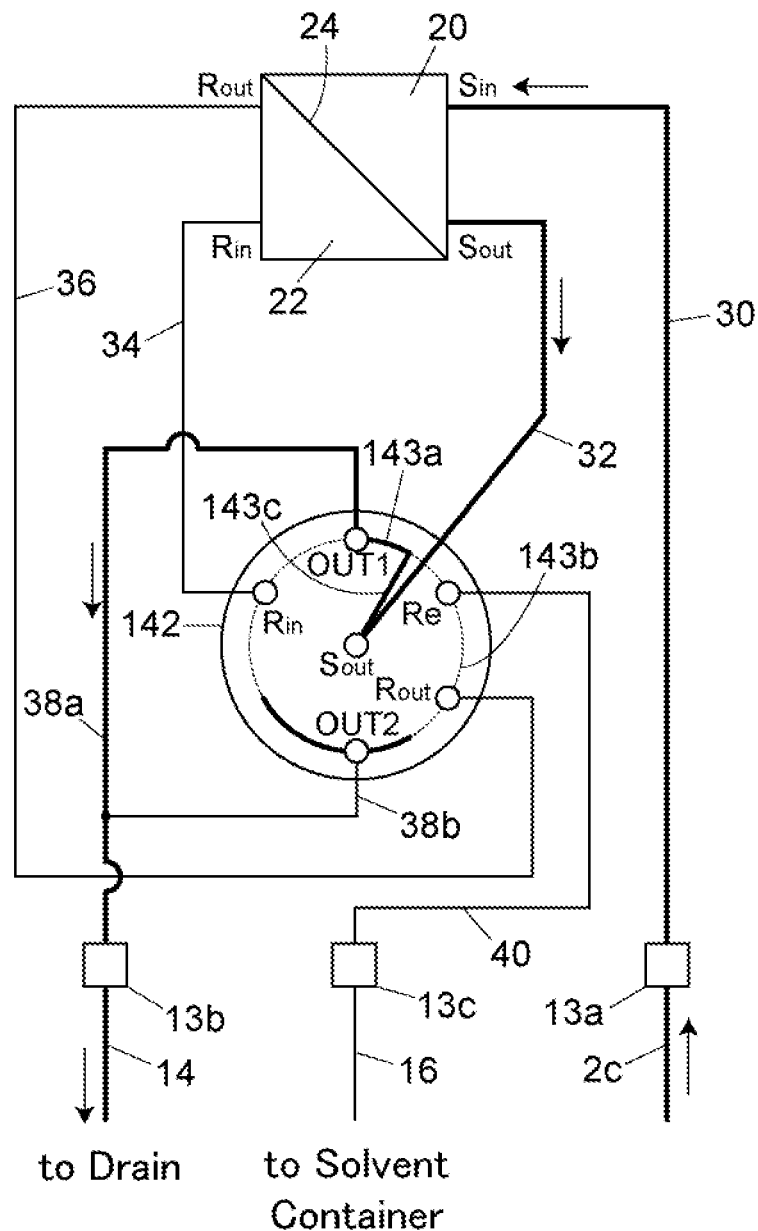
FIG. 10 is a diagram showing a channel structure of the present example at the time of the normal analysis mode.

As shown in FIG. 10, channels for the normal analysis mode are formed by placing the end portion of the groove 143a in the reverse direction at the position of the port (OUT1), and communicating the center port ($S_{out}$) and the port (OUT1) by the grooves 143a and 143c. As shown by thick lines in FIG. 10, according to such a channel structure, a liquid flowing out of the sample cell 20 is discharged to the drain via the channel 32, the groove 143c, the groove 143a, the channel 38a, the first outlet port 13b, and the channel 14.

Figure 11:
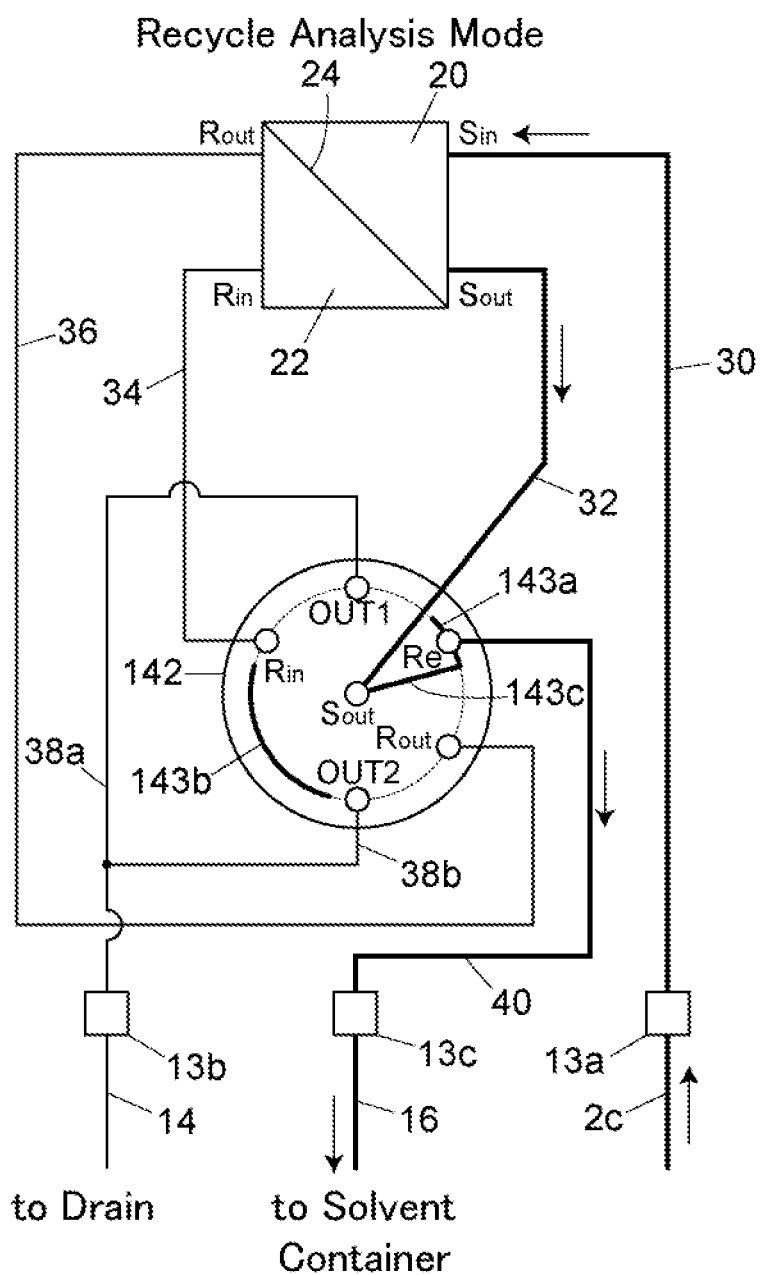
FIG. 11 is a diagram showing a channel structure of the present example at the time of the recycle analysis mode.

As shown in FIG. 11, channels for the recycle analysis mode are formed by causing the rotor of the switching valve 142 to be at a position that is rotated from the position in the normal analysis mode in the forward direction by 45 degrees, that is, by causing a center portion of the groove 143a to be at the position of the port (Re), and the groove 143b to be between the port ($R_{in}$) and the port (OUT2). The center port ($S_{out}$) and the port (Re) are communicated by the grooves 143a and 143c. As shown by thick lines in FIG. 11, according to such a channel structure, a liquid flowing out of the sample cell 20 is returned to the solvent container 6 via the channel 32, the groove 143c, the groove 143a, the channel 40, the second outlet port 13c, and the recycle channel 16.

What is claimed is:

1. A refractive index detector comprising:
   a sample cell, made of a light transmitting container, including a sample cell inlet through which a liquid flows in, and a sample cell outlet through which a liquid flows out;
   a reference cell, made of a light transmitting container, including a reference cell inlet through which a liquid flows in, and a reference cell outlet through which a liquid flows out, the reference cell being arranged adjacent to the sample cell across a light transmitting partition wall;
   a measurement section including a light source for emitting light in such a way that the light passes through both of the sample cell and the reference cell from a side of one of the cells, and a photodetector for detecting displacement of the light which has passed through the sample cell and the reference cell;
   a liquid inlet port that leads to the sample cell inlet;
   a first outlet port for discharging a liquid;
   a second outlet port for discharging a liquid, provided separately from the first outlet port; and
   a switching mechanism including a reference liquid supply mode for forming a channel for connecting the reference cell outlet to one of the first outlet port and the second outlet port while connecting the sample cell outlet to the reference cell inlet, and an analysis mode for forming a channel for connecting the sample cell outlet to one of the first outlet port and the second outlet port while sealing the reference cell outlet;
   wherein a recycle channel for returning a liquid to a liquid supply section is to be connected to the second outlet port, and
   wherein the switching mechanism includes, as the reference liquid supply mode, a reference liquid normal supply mode for connecting the reference cell outlet to the first outlet port while connecting the sample cell outlet to the reference cell inlet, and a reference liquid recycled supply mode for connecting the reference cell outlet to the second outlet port while connecting the sample cell outlet to the reference cell inlet, and includes, as the analysis mode, a normal analysis mode for connecting the sample cell outlet to the first outlet port while sealing the reference cell outlet, and a recycle analysis mode for connecting the sample cell outlet to the second outlet port while sealing the reference cell outlet.

2. A liquid chromatograph comprising:
   a delivery pump for suction a solvent from a solvent container storing the solvent, and delivering the solvent;
   an analysis channel for delivering, as a mobile phase, the solvent taken in from the solvent container by the delivery pump;
   a sample introduction section provided on the analysis channel, on a downstream side of the delivery pump, the sample injection section being for introducing a sample into the analysis channel;
   an analytical column provided on the analysis channel, on a downstream side of the sample introduction section, the analytical column being for separating the sample introduced into the analysis channel by the sample introduction section into sample components;
   a refractive index detector according to claim 1, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and
   a recycle channel connecting the second outlet port of the refractive index detector and the solvent container, the recycle channel being for returning a liquid flowing out of the second outlet port to the solvent container.

3. The refractive index detector according to claim 1, further comprising a control section for controlling an operation of the switching mechanism, the control section including a recycle analysis operation section for placing, based on a detection signal of the photodetector of the measurement section, the switching mechanism in the normal analysis mode when a sample is detected during analysis of the sample, and in the recycle analysis mode when a sample is not detected.

4. A liquid chromatograph comprising:
a delivery pump for suction a solvent from a solvent container storing the solvent, and delivering the solvent;
an analysis channel for delivering, as a mobile phase, the solvent taken in from the solvent container by the delivery pump;
a sample introduction section provided on the analysis channel, on a downstream side of the delivery pump, the sample injection section being for introducing a sample into the analysis channel;
an analytical column provided on the analysis channel, on a downstream side of the sample introduction section, the analytical column being for separating the sample introduced into the analysis channel by the sample introduction section into sample components;
a refractive index detector according to claim 3, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and
a recycle channel connecting the second outlet port of the refractive index detector and the solvent container, the recycle channel being for returning a liquid flowing out of the second outlet port to the solvent container.

5. The refractive index detector according to claim 1, wherein the switching mechanism is configured by one rotary switching valve including ports to which the sample cell outlet, the reference cell inlet, the reference cell outlet, the first outlet port, and the second outlet port are connected, and a rotor for switching a connection between ports by rotating, the rotor being provided with a groove for connecting the ports.

6. A liquid chromatograph comprising:
a delivery pump for suction a solvent from a solvent container storing the solvent, and delivering the solvent;
an analysis channel for delivering, as a mobile phase, the solvent taken in from the solvent container by the delivery pump;
a sample introduction section provided on the analysis channel, on a downstream side of the delivery pump, the sample injection section being for introducing a sample into the analysis channel;
an analytical column provided on the analysis channel, on a downstream side of the sample introduction section, the analytical column being for separating the sample introduced into the analysis channel by the sample introduction section into sample components;
a refractive index detector according to claim 5, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and
a recycle channel connecting the second outlet port of the refractive index detector and the solvent container, the recycle channel being for returning a liquid flowing out of the second outlet port to the solvent container.

7. The refractive index detector according to claim 5, wherein the switching valve includes one center port and a plurality of circumferential ports arranged on a circumference having the center port as a center, where the rotor includes two grooves provided in a circumferential direction so as to connect adjacent ports of the circumferential ports, and one groove provided in a radial direction so as to connect the center port and one of the circumferential ports.

8. A liquid chromatograph comprising:
a delivery pump for suction a solvent from a solvent container storing the solvent, and delivering the solvent;
an analysis channel for delivering, as a mobile phase, the solvent taken in from the solvent container by the delivery pump;
a sample introduction section provided on the analysis channel, on a downstream side of the delivery pump, the sample injection section being for introducing a sample into the analysis channel;
an analytical column provided on the analysis channel, on a downstream side of the sample introduction section, the analytical column being for separating the sample introduced into the analysis channel by the sample introduction section into sample components;
a refractive index detector according to claim 7, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and
a recycle channel connecting the second outlet port of the refractive index detector and the solvent container, the recycle channel being for returning a liquid flowing out of the second outlet port to the solvent container.

9. The refractive index detector according to claim 7, wherein, at the switching valve, the sample cell outlet, the reference cell inlet, the reference cell outlet, and the first outlet port are connected to the circumferential ports, the second outlet port is connected to the center port, the reference cell inlet and the first outlet port are connected to ports adjacent to the port to which the sample cell outlet is connected, and the port to which the reference cell outlet is connected and the port to which the first outlet port is connected are adjacent to each other.

10. A liquid chromatograph comprising:
a delivery pump for suction a solvent from a solvent container storing the solvent, and delivering the solvent;
an analysis channel for delivering, as a mobile phase, the solvent taken in from the solvent container by the delivery pump;
a sample introduction section provided on the analysis channel, on a downstream side of the delivery pump, the sample injection section being for introducing a sample into the analysis channel;
an analytical column provided on the analysis channel, on a downstream side of the sample introduction section, the analytical column being for separating the sample introduced into the analysis channel by the sample introduction section into sample components;

a refractive index detector according to claim 9, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and a recycle channel connecting the second outlet port of the refractive index detector and the solvent container, the recycle channel being for returning a liquid flowing out of the second outlet port to the solvent container.

11. The refractive index detector according to claim 7, wherein the switching valve includes, as the circumferential ports, one port to which the reference cell inlet is connected, one port to which the reference cell outlet is connected, two ports to which the first outlet port is connected, and one port to which the second outlet port is connected, and also includes, as the center port, a port to which the sample cell outlet is connected, and wherein, of the circumferential ports, the port to which the reference cell inlet is connected and the port to which the second outlet port is connected are adjacent to one of the ports to which the first outlet port is connected, and the port to which the second outlet port is connected and an other of the ports to which the first outlet port is connected are adjacent to the port to which the reference cell outlet is connected.

12. A liquid chromatograph comprising:

a delivery pump for suction a solvent from a solvent container storing the solvent, and delivering the solvent;

an analysis channel for delivering, as a mobile phase, the solvent taken in from the solvent container by the delivery pump;

a sample introduction section provided on the analysis channel, on a downstream side of the delivery pump, the sample injection section being for introducing a sample into the analysis channel;

an analytical column provided on the analysis channel, on a downstream side of the sample introduction section, the analytical column being for separating the sample introduced into the analysis channel by the sample introduction section into sample components;

a refractive index detector according to claim 11, provided on the analysis channel, on a downstream side of the analytical column, the refractive index detector including a liquid inlet port that is connected to an outlet of the analytical column, and a first outlet port and a second outlet port through which a liquid flows out, the refractive index detector being for detecting a sample component separated by the analytical column; and a recycle channel connecting the second outlet port of the refractive index detector and the solvent container, the recycle channel being for returning a liquid flowing out of the second outlet port to the solvent container.

* * * * *